(12) United States Patent
Bornzin et al.

(10) Patent No.: US 7,294,108 B1
(45) Date of Patent: Nov. 13, 2007

(54) CARDIAC EVENT MICRORECORDER AND METHOD FOR IMPLANTING SAME

(75) Inventors: Gene A. Bornzin, Simi Valley, CA (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 184 days.

(21) Appl. No.: 11/046,270

(22) Filed: Jan. 27, 2005

(51) Int. Cl.
*A61B 5/00* (2006.01)

(52) U.S. Cl. .............................. 600/300; 607/1; 607/2; 607/3; 600/377; 128/899

(58) Field of Classification Search ........ 600/508–509, 600/523, 377, 300; 607/523, 2, 1–3; 128/899
See application file for complete search history.

(56) References Cited

U.S. PATENT DOCUMENTS

| | | | |
|---|---|---|---|
| 4,026,300 A | 5/1977 | DeLuca et al. ............. 128/418 |
| 4,573,481 A | 3/1986 | Bullara ....................... 128/784 |
| 4,590,946 A | 5/1986 | Loeb .......................... 128/642 |
| 4,920,979 A | 5/1990 | Bullara ....................... 128/784 |
| 4,934,368 A | 6/1990 | Lynch ..................... 128/419 R |
| 4,947,858 A | 8/1990 | Smith ......................... 128/696 |
| 5,127,404 A | 7/1992 | Wyborny et al. ........ 128/419 P |
| 5,193,539 A | 3/1993 | Schulman et al. ...... 128/419 R |
| 5,193,540 A | 3/1993 | Schulman et al. ...... 128/419 R |
| 5,312,446 A | 5/1994 | Holschbach et al. ............ 607/9 |
| 5,324,316 A | 6/1994 | Schulman et al. ............ 607/61 |
| 5,358,514 A | 10/1994 | Schulman et al. ............ 607/61 |
| 5,405,367 A | 4/1995 | Schulman et al. ............ 607/61 |
| 5,782,876 A | 7/1998 | Flammang ..................... 607/4 |
| 5,851,221 A | 12/1998 | Rieder et al. ................. 607/93 |
| 6,164,284 A * | 12/2000 | Schulman et al. .......... 128/899 |
| 6,185,455 B1 * | 2/2001 | Loeb et al. ..................... 607/3 |
| 6,230,059 B1 | 5/2001 | Duffin .......................... 607/60 |
| 6,240,316 B1 | 5/2001 | Richmond et al. ............ 607/42 |
| 6,582,441 B1 * | 6/2003 | He et al. ..................... 606/129 |
| 6,733,485 B1 * | 5/2004 | Whitehurst et al. ......... 604/500 |
| 6,735,474 B1 * | 5/2004 | Loeb et al. ................... 607/41 |
| 2002/0072785 A1 | 6/2002 | Nelson et al. ................ 607/60 |
| 2003/0078643 A1 * | 4/2003 | Schulman et al. .......... 607/116 |
| 2003/0114769 A1 | 6/2003 | Loeb et al. ................. 600/513 |
| 2003/0233126 A1 * | 12/2003 | Kaplan et al. .................. 607/3 |
| 2004/0153127 A1 * | 8/2004 | Gordon et al. .................. 607/1 |
| 2005/0245969 A1 * | 11/2005 | Loeb ............................. 607/2 |

FOREIGN PATENT DOCUMENTS

| | | |
|---|---|---|
| EP | 1464362 A1 | 10/2004 |
| WO | WO 98/02209 A2 | 1/1998 |
| WO | WO 98/02209 A3 | 1/1998 |

\* cited by examiner

*Primary Examiner*—Carl Layno
*Assistant Examiner*—Shevon E Johnson

(57) ABSTRACT

A cardiac event microrecorder comprising a hermetically sealed housing is shaped and dimensioned to facilitate the subcutaneous implantation of the microrecorder in a human patient by injection through the lumen of a hypodermic needle. The housing comprises a tubular central section of an electrically insulating material, the central section having spaced apart extremities. An electrically conductive sense electrode is secured to and seals each extremity. The housing may have an interior enclosing (1) electrical circuitry for processing, storing and telemetering data representing physiologic information detected by the sense electrodes; (2) a primary cell or rechargeable battery for electrically powering the electrical circuitry; and (3) an inductively couplable charger where a rechargeable battery is used. Also disclosed are a method of subcutaneously implanting a cardiac event recorder in a patient's thoracic region, and a handheld mapping device for determining an optimum location and orientation for the cardiac event microrecorder to be implanted.

6 Claims, 8 Drawing Sheets

CARDIAC EVENT MICRORECORDER AND METHOD FOR IMPLANTING SAME

FIELD OF THE INVENTION

The present invention relates generally to implantable medical devices, and more particularly to an implantable microrecorder for monitoring cardiac events such as heart rate and rhythm.

BACKGROUND OF THE INVENTION

A Holter monitor, comprising electrodes placed on a patient's chest area and attached to a recorder carried externally by the patient, provides a continuous electrocardiograph (EKG) of heart rhythm for a pre-determined period, for example, 24 hours. Certain precautions must be observed. For example, the electrodes must not be touched, adjusted or subjected to moisture. The externally worn Holter monitor with the attached skin electrodes tends to be both inconvenient and uncomfortable.

The Medtronic Reveal® insertible loop recorder is an attempt to overcome some of the disadvantages of the Holter monitor. The Medtronic recorder is a subcutaneously implantable device having a pair of spaced-apart sense electrodes for detecting cardiac far field electrograms. However, the device is relatively bulky and its subcutaneous implantation necessitates significant surgery.

Implantable, microminiature, radio-telemetrically operated sensors injectable through the lumen of a hypodermic-type needle have been developed for small animal research. These sensors receive their power wirelessly from an external power source via a radio frequency magnetic field inductively coupling a coil on the external power source with a coil within the implant. Accordingly, the animal must be maintained in close proximity to the external power source.

There continues to be a need for a minimally invasive cardiac event recorder that is easily implantable in a human body, is completely self-contained and automatically senses and records cardiac events for subsequent retrieval and analysis with minimum discomfort and inconvenience to the patient.

SUMMARY

In accordance with one specific exemplary embodiment, there is provided a medical microrecorder comprising a hermetically sealed housing shaped and dimensioned to facilitate the subcutaneous implantation of the microrecorder in a human patient by injection through the lumen of a hypodermic needle. In one form, the housing may comprise a tubular central section made of an electrically insulating material. The central section has a pair of spaced apart extremities and further comprises an electrically conductive sense electrode secured to and sealing each extremity.

Pursuant to another illustrative embodiment, the housing may have an interior enclosing electrical circuitry for processing, storing and telemetering data representing physiologic information detected by the sense electrodes. The housing may further enclose a battery for electrically powering the circuitry. In accordance with one embodiment, the battery may comprise a primary cell. Alternatively, the battery may comprise a rechargeable battery, in which case the interior of the housing may also enclose a battery charger connected to charge the rechargeable battery. The charger may be adapted to be powered transcutaneously from an external electrical power source via the telemetering circuitry.

In accordance with a further illustrative embodiment, each of the sense electrodes of the microrecorder may comprises a cup-shaped element having an open end and a closed end, the open end of the electrode having a surface configured to sealingly engage a corresponding surface on the central section of the housing.

BRIEF DESCRIPTION OF THE DRAWINGS

The foregoing and other objects, features and advantages of the invention will become evident to those skilled in the art from the detailed description of the preferred embodiments, below, taken together with the accompanying drawings, in which.

DETAILED DESCRIPTION

The following description presents preferred embodiments of the invention representing the best mode contemplated for practicing the invention. This description is not to be taken in a limiting sense but is made merely for the purpose of describing the general principles of the invention whose scope is defined by the appended claims.

In accordance with preferred embodiments, the cardiac event microrecorder of the present invention is a completely self-contained, minimally invasive device configured and dimensioned so as to facilitate its delivery subcutaneously by injecting it through the lumen of a hypodermic needle into a human body, for example, into the upper left thoracic region. The microrecorder automatically senses and records various cardiac events and, when interrogated, may wirelessly transmit the recorded information to an external programmer by means of an RF telemetry link. By way of example, the microrecorder may be sensitive to and record arrhythmia episodes such as tachycardia, bradycardia, and PVC's (premature ventricular contractions) while discriminating against extraneous signals such as electromyographic noise signals generated by adjacent chest muscle so that it only responds to and stores far field electrocardiographic signals.

Figure 1:
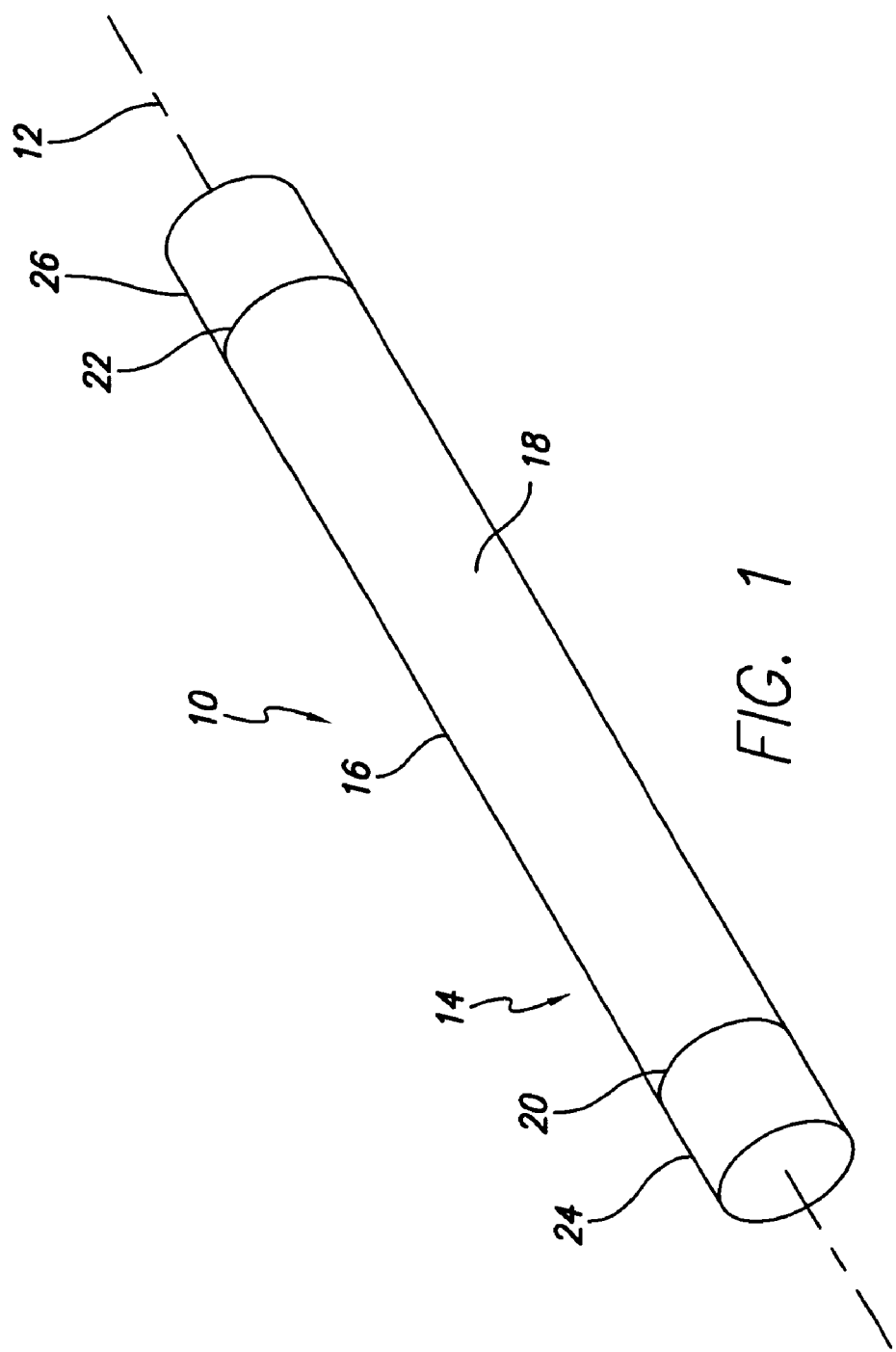
FIG. 1 is a perspective view of a microrecorder in accordance with one specific exemplary embodiment of the invention.
Figure 2:
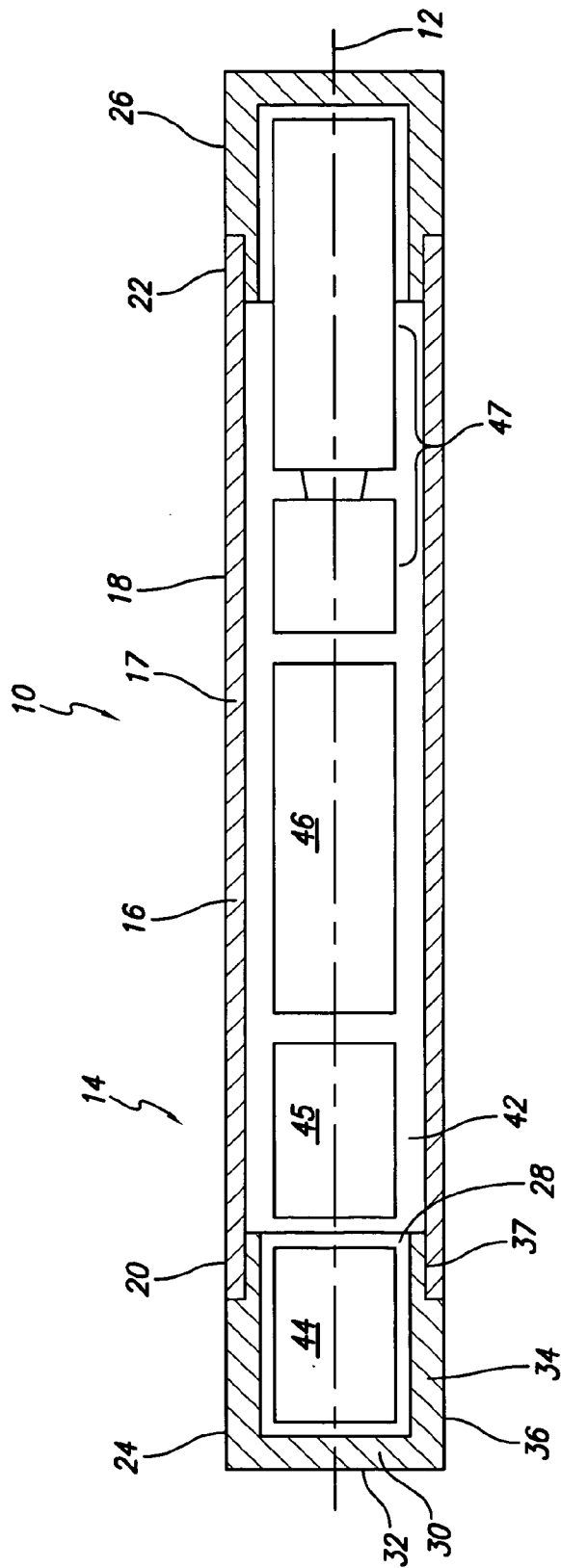
FIG. 2 is an axial cross section view of the microrecorder shown in FIG. 1.

With reference to FIGS. 1 and 2, there is shown an exemplary embodiment of the present invention comprising a self-contained, cardiac event microrecorder 10 configured and dimensioned to facilitate its subcutaneous implantation in a human patient by injecting it through the lumen of a hypodermic needle. The microrecorder 10 may have a generally cylindrical configuration with a diameter less than 6 mm and a length less than 50 mm. More preferably, the microrecorder 10 may have a diameter ranging from 0.6 to 6 mm, and a length ranging from 5 to 50 mm. Most preferably, the microrecorder may have a diameter of 3 mm and a length of 30 mm.

The microrecorder 10 has a central, longitudinal axis 12 and comprises a housing 14 having a central tubular section 16 fabricated from a biocompatible, biostable, insulating material such as a ceramic, a glass, or a polymer. The central tubular section 16 has a side wall 17, an outer cylindrical surface 18 and opposed ends 20 and 22. The housing 14 of the microrecorder further includes preferably identical sense electrodes 24 and 26 at the ends 20 and 22, respectively. The interelectrode spacing is determined by the length of the housing, as specified above. Each of the sense electrodes 24 and 26 is preferably fabricated of an electrically conductive, biostable, biocompatible material such as a noble metal or titanium, or of an alloy such as platinum/iridium, stainless steel, or the like, or silver chloride covered with a semipermeable membrane such as a cation exchange membrane or an ion permeable membrane such as Gortex®. (The term "noble metal" is used herein in its accepted sense as comprising gold, silver and the platinum group, namely, platinum, rhodium, palladium, ruthenium, osmium and iridium.)

In the embodiment of FIGS. 1 and 2, each of the sense electrodes 24 and 26 has a generally cup-shaped or cap configuration. Taking the electrode 24 as representative, this electrode includes an open end 28, a closed end 30 comprising a transverse, generally planar end wall 32, and a side wall 34 having an outer cylindrical surface 36 flush with the outer cylindrical surface 18 of the central tubular section 16. By way of example, the outer cylindrical surface 36 may have a length ranging from 1 to 5 mm. The side wall 34, which is preferably thicker than the side wall 17 of the central tubular section 16, has a step 37 formed therein adjacent to the open end 28 for receiving the end 20 of the tubular section in overlapping fashion. The abutting surfaces of the tubular section 16 and the electrode 24 are bonded by, for example, brazing or an appropriate adhesive bonding material such as an epoxy. The sense electrode 26 is similarly configured and secured to the central tubular section 16. Thus, there is formed a hermetically sealed enclosure having a smooth, continuous outer surface and defining a housing interior 42.

Contained within the interior 42 of the housing 14 are electrical components including an amplifier/signal processing/analog-to-digital converter unit 44; a telemetry unit 45 forming part of a transcutaneous RF telemetry system; a logic/memory/microprocessor unit 46; and an electrical power unit 47. It will be appreciated that the microrecorder of the invention is a completely self-contained device, including its own battery power supply thereby providing a unit that is small and mobile, eliminating the need for the microrecorder to remain in the proximity of a magnetically coupled power unit; such proximity is only required during the short intervals for recharging the battery (where a rechargeable battery is used), and when data is downloaded.

Figure 3:
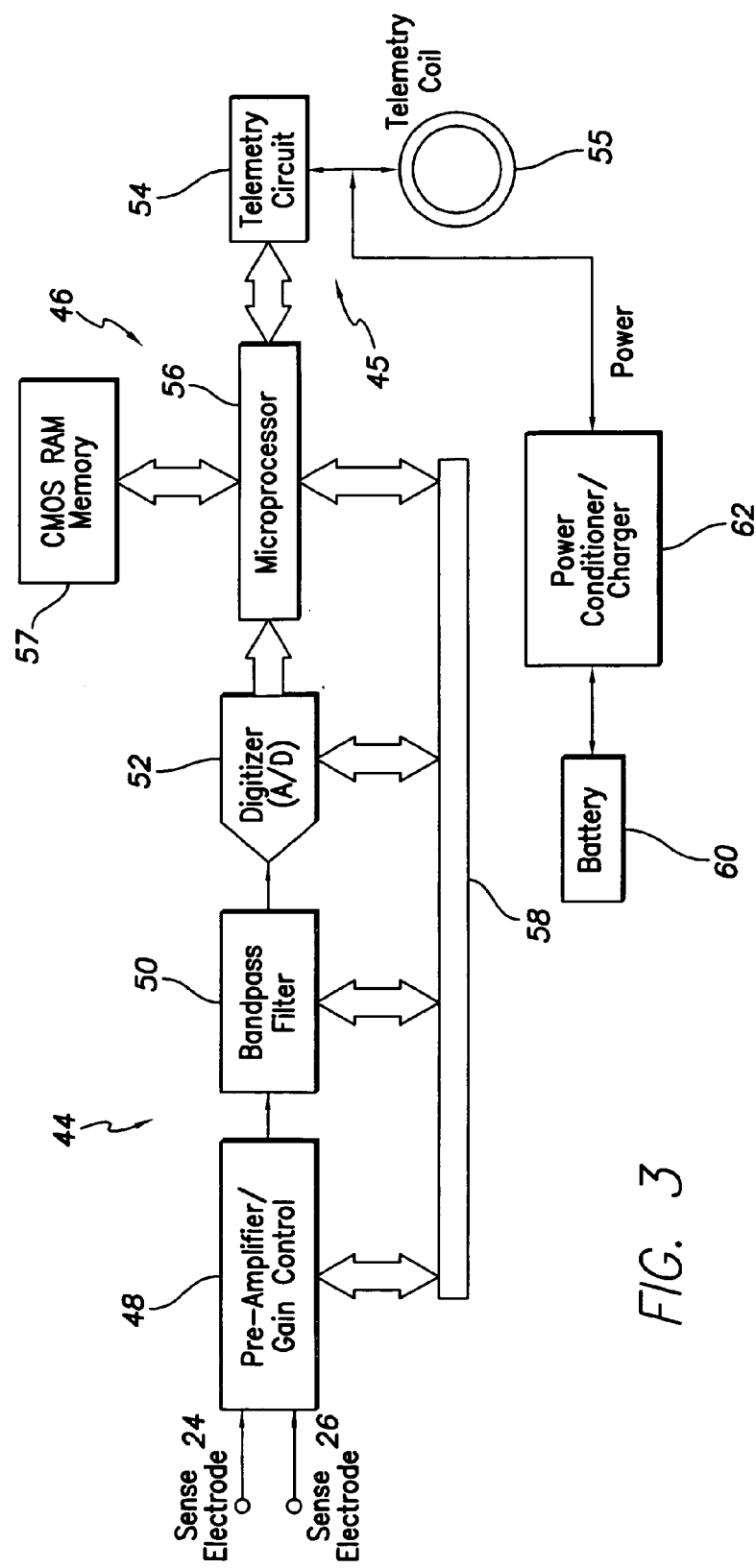
FIG. 3 is a block diagram of a preferred embodiment of the electronic circuitry of the microrecorder shown in FIG. 1.

FIG. 3 depicts in schematic form an exemplary embodiment of the principal electronic units 44-47 enclosed within the housing of the microrecorder. The unit 44 comprises a programmable preamplifier 48 connected to receive from the sense electrodes 24 and 26 electrical signals representing the physiologic variables of interest; a bandpass filter 50; and an analog-to-digital converter (ADC) 52. The unit 45 comprises a telemetry circuit 54 and a telemetry coil 55 and the unit 46 comprises a microprocessor 56 and a digital memory 57, preferably low power consumption CMOS RAM. These components, as well as their interconnections and operation, are well known in the art. Control and status signals are transmitted along a bus 58 interconnecting the microprocessor, programmable preamplifier, bandpass filter and ADC. The electrical power unit 47 comprises a battery 60 whose output is filtered, regulated and otherwise appropriately conditioned by a power conditioner and battery charger 62, periodically coupled telemetrically via the telemetry unit 45 to an external power source for recharging the battery, where a rechargeable battery is utilized. The power conditioner and charger 62 may also be adapted to provide a charge status signal to an indicator to prevent overcharging.

It will be appreciated that the electrical components may be mounted on one or more substrates and arranged physically within the housing 14 in any fashion that optimizes the compactness of the assembly. The linear arrangement of the components shown schematically in FIG. 2 will be understood to be exemplary only.

The battery 60 may comprise a primary (non-rechargeable) cell or a rechargeable battery, preferably of the lithium type in either case. Programming of the microrecorder may be effected in well known fashion by a downloaded, transcutaneous, telemetered transmission from an external programmer. The data stored in the memory 57 of the microrecorder may be uploaded by transcutaneous, telemetered transmission to the external programmer for display and analysis.

The external part of the battery charger may be integrated with the data download inductive coupling, or may be separate therefrom. Since data download tends to be a more time-consuming operation, for efficiency, data download and battery recharge may be performed simultaneously. It will be evident that, in accordance with techniques well known in the art, the system may be arranged to permit the patient to download the data and telephonically transmit the data to a data collection center, a physician's office, or to a website, via a wired or wireless link.

Figure 4:
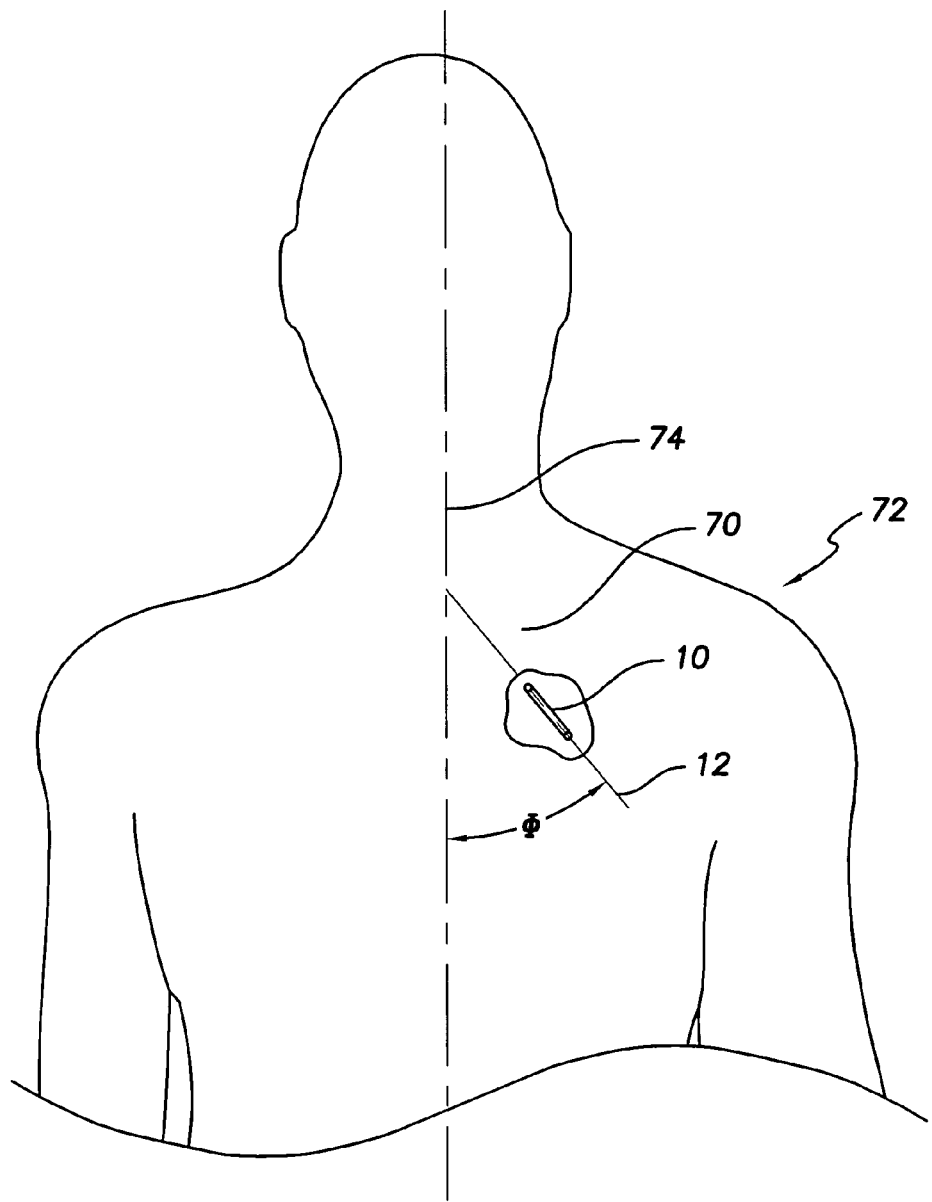
FIG. 4 is a front view, partly cut away, of a human patient's thoracic region showing the microrecorder of FIGS. 1-3 implanted subcutaneously therein.

FIG. 4 shows the cardiac event microrecorder 10 of FIGS. 1-3 implanted subcutaneously in the left upper thoracic region 70 of a patient's body 72. The size of the microrecorder 10 in relation to the thoracic region 70 as depicted in FIG. 4 has been expanded for clarity; the microrecorder would actually appear substantially smaller relative to the patient's body. Prior to injection of the microrecorder 10, a mapping device, described below, is moved along the surface of a preferably cleaned area of the patient's skin in the thoracic region while monitoring its output to optimize the implant location and orientation of the microrecorder. The skin may be cleaned using alcohol followed by, as an optional step, application of an abrasive pad. Next, an electrolyte gel may be applied to assure good electrical conduction. A small incision may then be made through which the microrecorder is inserted and positioned by means of a hypodermic needle. Alternatively, the hypodermic needle may be inserted directly without an entry incision. FIG. 4 shows one example in which the microrecorder 10 has been implanted in the patient's left upper thoracic region 70 with the longitudinal axis 12 of the microrecorder oriented at an angle, $\phi$, with respect to the body's medial plane 74.

Electrical far field signals generated by the depolarization/repolarization of the heart are sensed across the electrodes 24 and 26; these signals are amplified, filtered and otherwise processed for storage in the memory and later retrieval transcutaneously via the telemetry circuit and coil.

Figure 5:
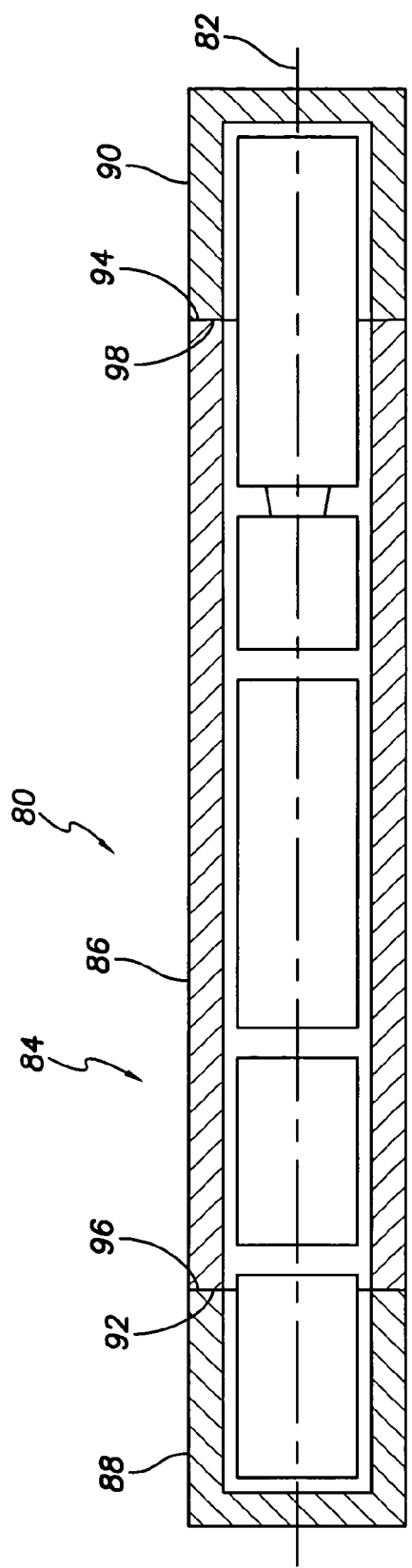
FIG. 5 is an axial cross section view of a microrecorder in accordance with an alternative embodiment of the invention.

FIG. 5 shows a microrecorder 80 in accordance with an alternative embodiment of the invention. The microrecorder 80 has a longitudinal axis 82 and comprises a housing 84 including a central tubular section 86 and preferably identical, cup-shaped end sense electrodes 88 and 90. The housing has radially extending planar end surfaces 92 and 94 abutting and bonded to corresponding planar end surfaces 96 and 98, respectively, on the sense electrodes 88 and 90. Bonding may be effected, for example, by brazing or by an epoxy to form a hermetically sealed housing enclosure. Other than the butt joint interfaces between the tubular section 86 and the sense electrodes 88 and 90 and the fact that the wall thicknesses of the tubular section and the sense electrodes may be the same, the embodiment of FIG. 5 is identical to that of FIGS. 1-3.

Figure 6:
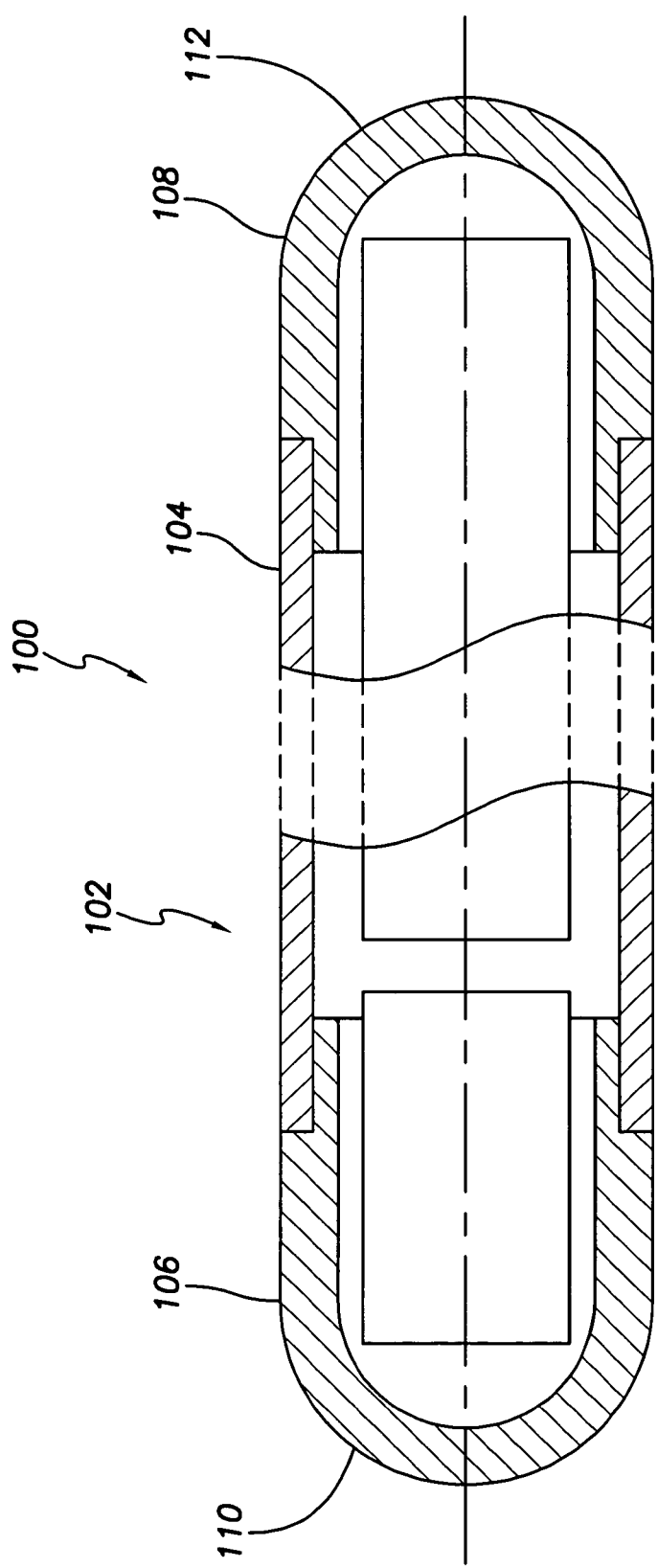
FIG. 6 is an axial cross section view of a portion of a microrecorder in accordance with another alternative embodiment of the invention.

FIG. 6 shows another alternative embodiment of the invention comprising a microrecorder 100 having a housing 102 including a central tubular housing 104 carrying preferably identical end sense electrodes 106 and 108. This embodiment may be identical to that of FIGS. 1-3 except that the sense electrodes 106 and 108, instead of having flat end surfaces, are provided with curved, for example, hemispherical, end surfaces 110 and 112, respectively, for greater patient comfort.

Figure 7:
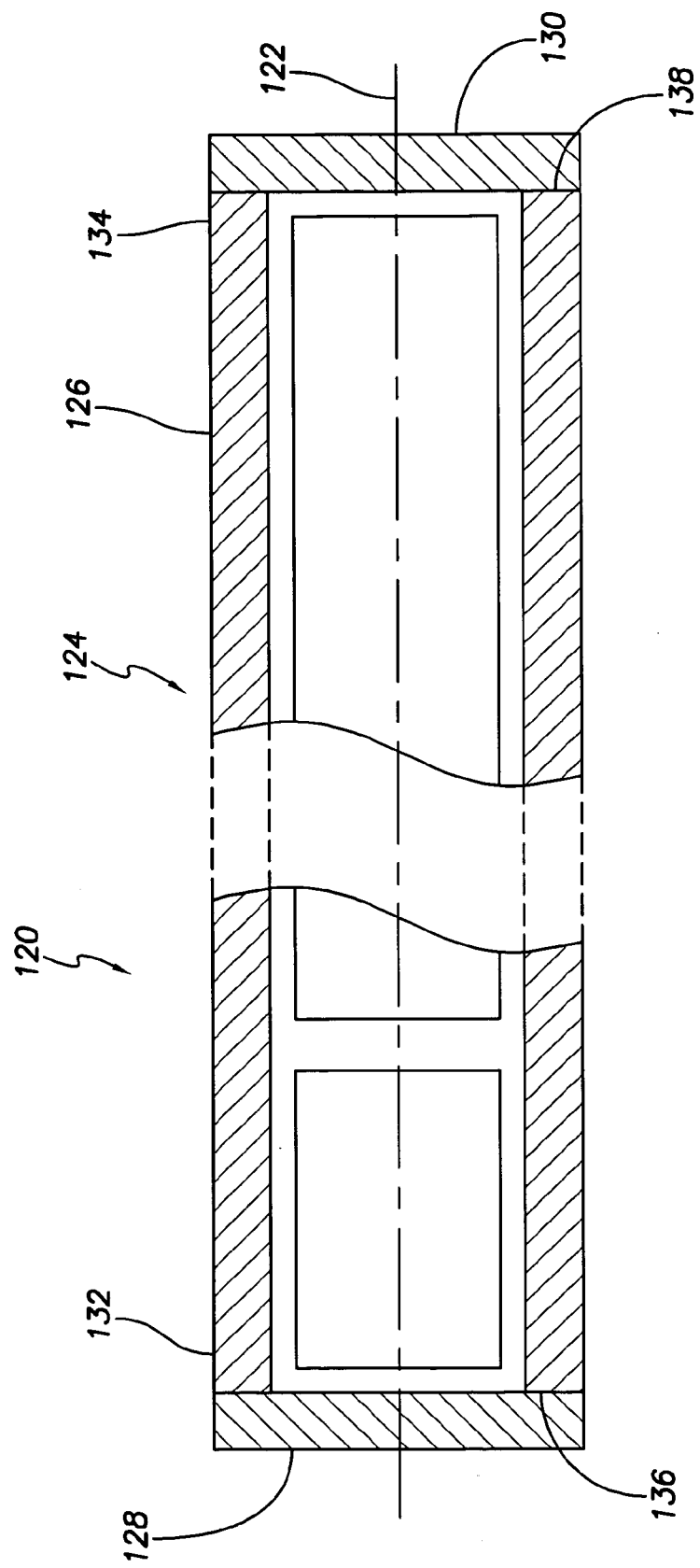
FIG. 7 is an axial cross section view of a portion of a microrecorder in accordance with yet another alternative embodiment of the invention.

FIG. 7 illustrates yet another alternative embodiment of the invention comprising a microrecorder 120 having a longitudinal axis 122 and including a housing 124 comprising a central tubular section 126 carrying preferably identical sense electrodes 128 and 130 at opposite ends 132 and 134, respectively, of the tubular section 126. This embodiment may be identical to that of FIG. 5 except that instead of cup-shaped sense electrodes, the sense electrodes 128 and 130 comprise radially oriented disks bonded, in a fashion previously described, to radially extending planar surfaces 136 and 138, respectively, formed on the opposite ends 132 and 134 of the tubular section 126.

Figure 8:
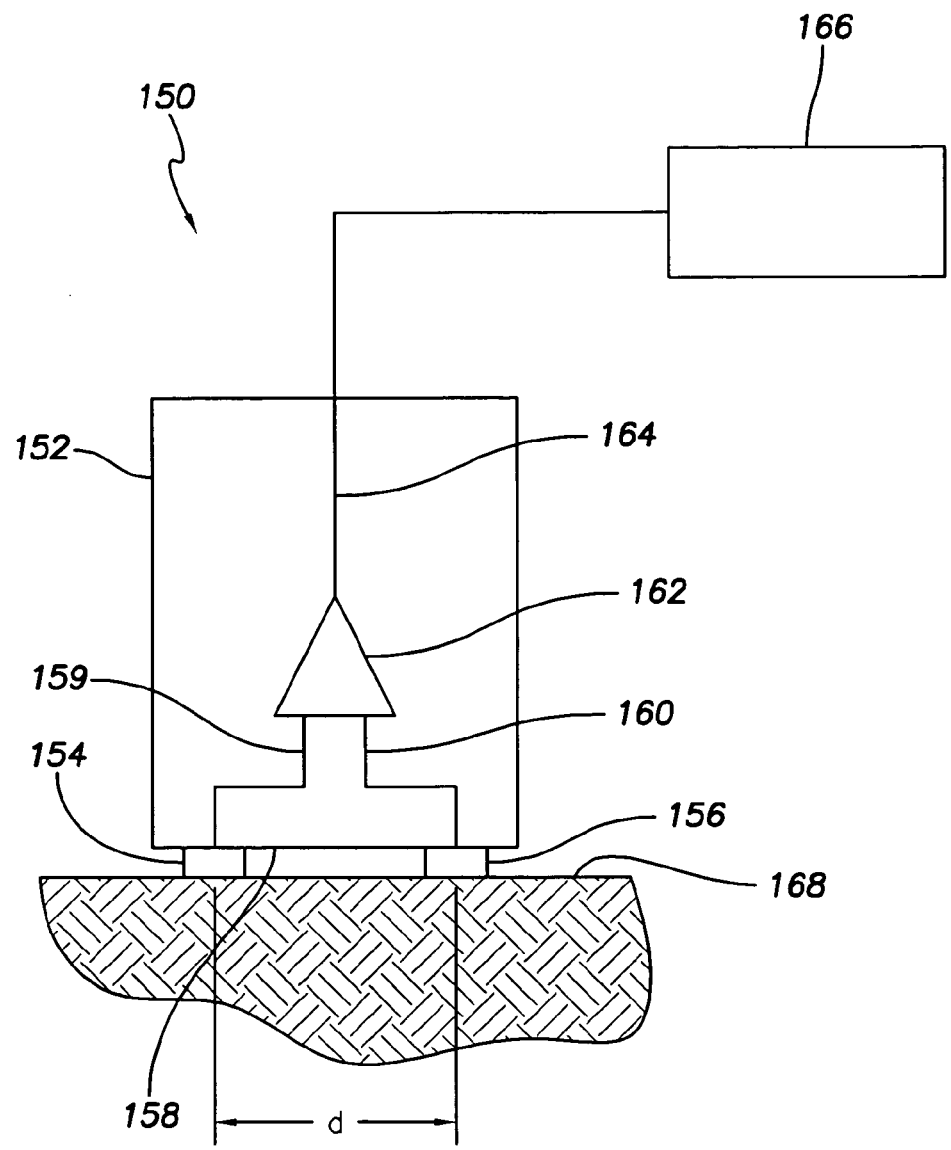
FIG. 8 is a diagrammatic representation of a handheld electrocardiographic field mapping device in accordance with another aspect of the invention.

FIG. 8 shows another aspect of the present invention comprising a handheld testing device 150 for determining an optimum location and orientation of the microrecorder to be implanted in a human patient by mapping the far field electrical signals generated by the successive depolarizations and repolarizations of the heart. The device 150 comprises a casing 152 carrying a pair of sense electrodes 154 and 156 projecting from a surface 158 of the device. The sense electrodes 154 and 156 are spaced apart by a distance, d, preferably substantially equal to the interelectrode distance of the sense electrodes on the microrecorder to be implanted. Also preferably, the sense electrodes 154 and 156 may comprise, for example, silver/silver chloride electrodes. The sense electrodes 154 and 156 are connected as inputs 159 and 160, respectively, to electrical circuitry housed within the casing 152, comprising, for example, a preamplifier 162, having an output 164 coupled to an external programmer 166. With the sense electrodes 154 and 156 in electrical contact with the external surface 168 of the patient's skin preferably in the thoracic region, the device 150 is moved manually along the skin surface 168 (preferably cleaned, as described) to determine, using the programmer 166, an optimum location and orientation for the microrecorder to be implanted.

While several illustrative embodiments of the invention have been shown and described, numerous variations and alternative embodiments will occur to those skilled in the art. For example, the central section of the housing and associated sense electrodes may have configurations other than those specifically shown. Such variations and alternative embodiments are contemplated, and can be made without departing fro the spirit and scope of the invention as defined in the appended claims.

What is claimed is:

1. A method of implanting a telemetric cardiac event microrecorder subcutaneously in the thoracic region of a human patient, the microrecorder including a pair of spaced apart sense electrodes, the method comprising:
    moving a mapping device having a pair of sense electrodes having an interelectrode spacing substantially the same as that of the electrodes on the microrecorder along a surface of the patient's skin in the thoracic region in contact with the skin while monitoring the electrical output of the mapping device to determine a suitable location and orientation for said microrecorder; and
    implanting the microrecorder based upon the determination.

2. The method of claim 1 wherein determining a suitable location comprises determining an optimal location.

3. The method of claim 1 wherein implanting the microrecorder comprises:
    using a hypodermic needle, inserting said microrecorder at said location and in alignment with said orientation; and
    withdrawing said hypodermic needle after expulsion of said microrecorder.

4. A handheld mapping device for determining an optimum location and orientation of a cardiac event microrecorder to be implanted subcutaneously in a human patient, the microrecorder including a pair of sense electrodes having an interelectrode spacing, the device comprising:
    a casing; and
    a pair of sense electrodes projecting from a surface of the casing and having an interelectrode spacing substantially the same as that of the electrodes on the microrecorder.

5. The mapping device of claim 4 further comprising:
    electrical circuitry within the casing, said sense electrodes on the casing being electrically connected to inputs on the electrical circuitry, said circuitry having an output adapted to be connected to an external programmer.

6. The mapping device of claim 4 wherein:
    the sense electrodes projecting from said casing comprise silver/silver chloride electrodes.

* * * * *